United States Patent
Chin et al.

(10) Patent No.: US 8,251,963 B2
(45) Date of Patent: Aug. 28, 2012

(54) FLEXIBLE NEEDLE

(75) Inventors: Yem Chin, Burlington, MA (US); Paul Scopton, Winchester, MA (US); Robert DeVries, Northboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1948 days.

(21) Appl. No.: 11/297,786

(22) Filed: Dec. 8, 2005

(65) Prior Publication Data

US 2007/0135681 A1 Jun. 14, 2007

(51) Int. Cl.
*A61M 5/32* (2006.01)

(52) U.S. Cl. .................................... 604/272

(58) Field of Classification Search .......... 604/242–274, 604/158–162, 164.01, 164.12
See application file for complete search history.

(56) References Cited

U.S. PATENT DOCUMENTS

| | | | |
|---|---|---|---|
| 3,976,078 A | 8/1976 | Toriello | |
| 4,463,755 A | 8/1984 | Suzuki | |
| 5,322,505 A * | 6/1994 | Krause et al. | 604/24 |
| 5,441,483 A | 8/1995 | Avitall | |
| 5,573,520 A | 11/1996 | Schwartz et al. | |
| 5,741,429 A * | 4/1998 | Donadio et al. | 216/8 |
| 6,017,319 A | 1/2000 | Jacobsen et al. | |
| 6,162,202 A | 12/2000 | Sicurelli et al. | |
| 6,390,096 B1 | 5/2002 | Conrad et al. | |
| 6,702,791 B1 * | 3/2004 | Hilgers et al. | 604/274 |
| 6,855,132 B2 | 2/2005 | Van Tassel et al. | |
| 2003/0125709 A1 * | 7/2003 | Eidenschink | 604/524 |
| 2003/0208136 A1 * | 11/2003 | Mark et al. | 600/564 |
| 2003/0229321 A1 | 12/2003 | Simon | |
| 2004/0133124 A1 * | 7/2004 | Bates et al. | 600/564 |
| 2004/0243143 A1 | 12/2004 | Corcoran et al. | |
| 2005/0015072 A1 | 1/2005 | Engel et al. | |
| 2005/0216018 A1 * | 9/2005 | Sennett | 606/79 |
| 2005/0283125 A1 | 12/2005 | Barkhahn et al. | |
| 2006/0100687 A1 * | 5/2006 | Fahey et al. | 623/1.11 |
| 2006/0264904 A1 * | 11/2006 | Kerby et al. | 604/523 |

FOREIGN PATENT DOCUMENTS

| | | |
|---|---|---|
| EP | 1 170 027 | 1/2002 |
| EP | 1 222 937 | 7/2002 |
| JP | 57-190571 | 11/1982 |
| JP | 2003-534037 | 11/2003 |
| JP | 2005 137454 | 6/2005 |
| WO | 99 / 25419 | 5/1999 |
| WO | 99 / 59663 | 11/1999 |
| WO | 2004/064898 | 8/2004 |

* cited by examiner

*Primary Examiner* — Theodore Stigell

(74) *Attorney, Agent, or Firm* — Fay Kaplun & Marcin, LLP

(57) ABSTRACT

An endoscopic instrument comprises a first flexible insertion member sized for insertion through a body lumen to a target site and a needle coupled to the insertion member for penetration of tissue, the needle including a plurality of flexibility enhancing grooves formed therein along at least a first portion of the length of the needle.

20 Claims, 3 Drawing Sheets

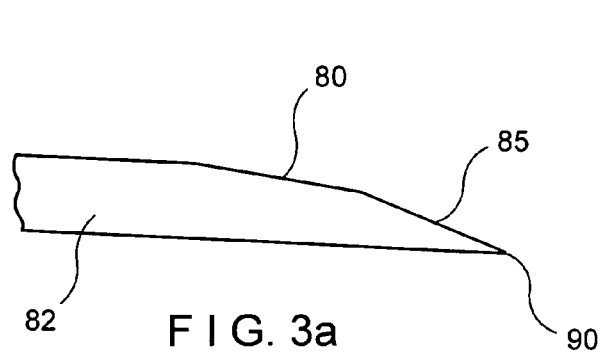
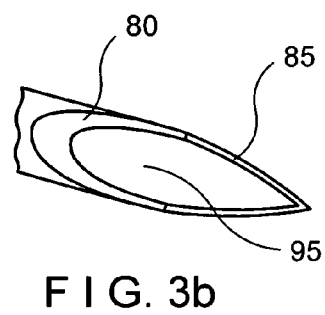
FIG. 3a
FIG. 3b
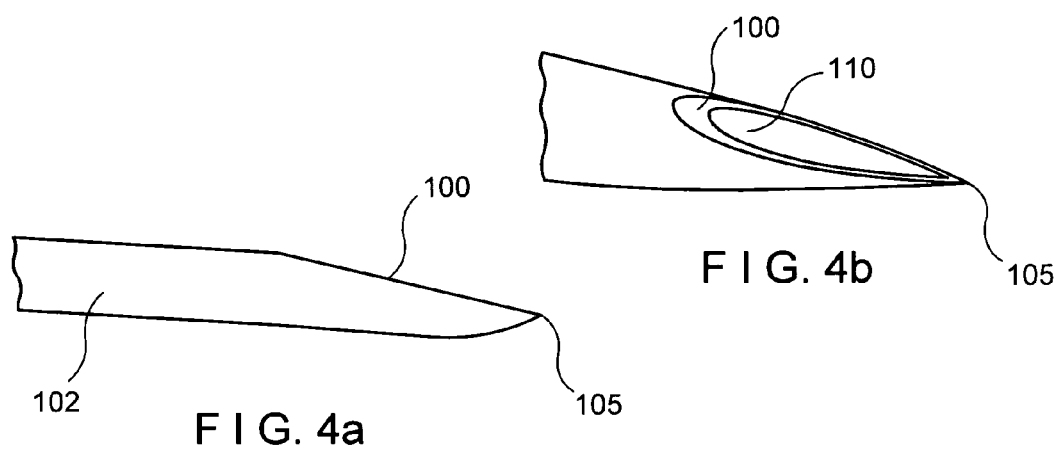
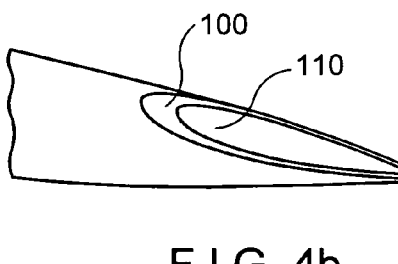
FIG. 4a
FIG. 4b
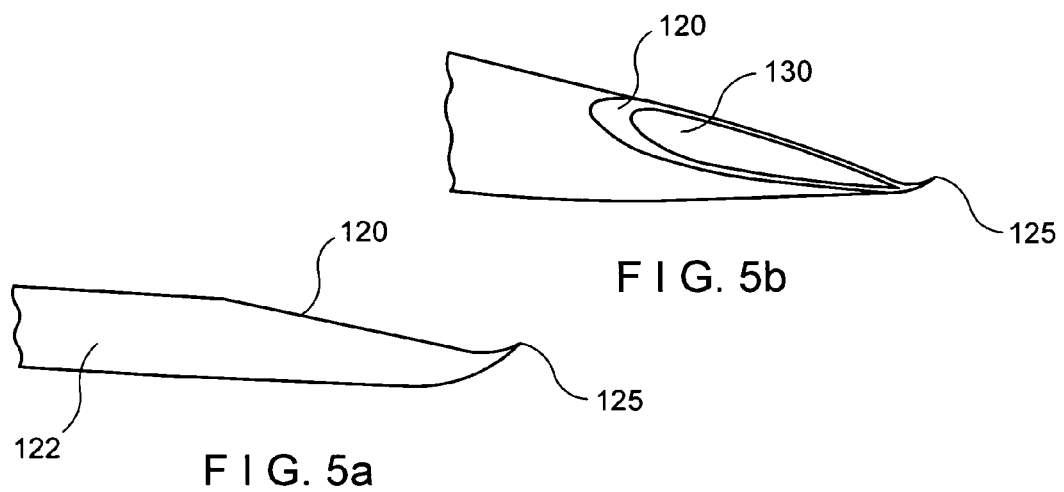
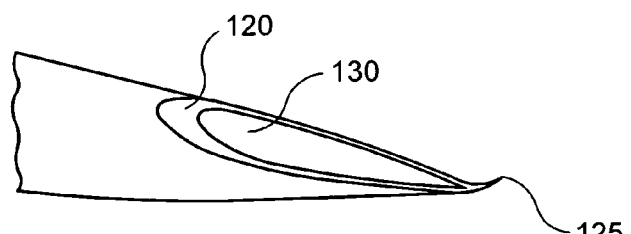
FIG. 5a
FIG. 5b

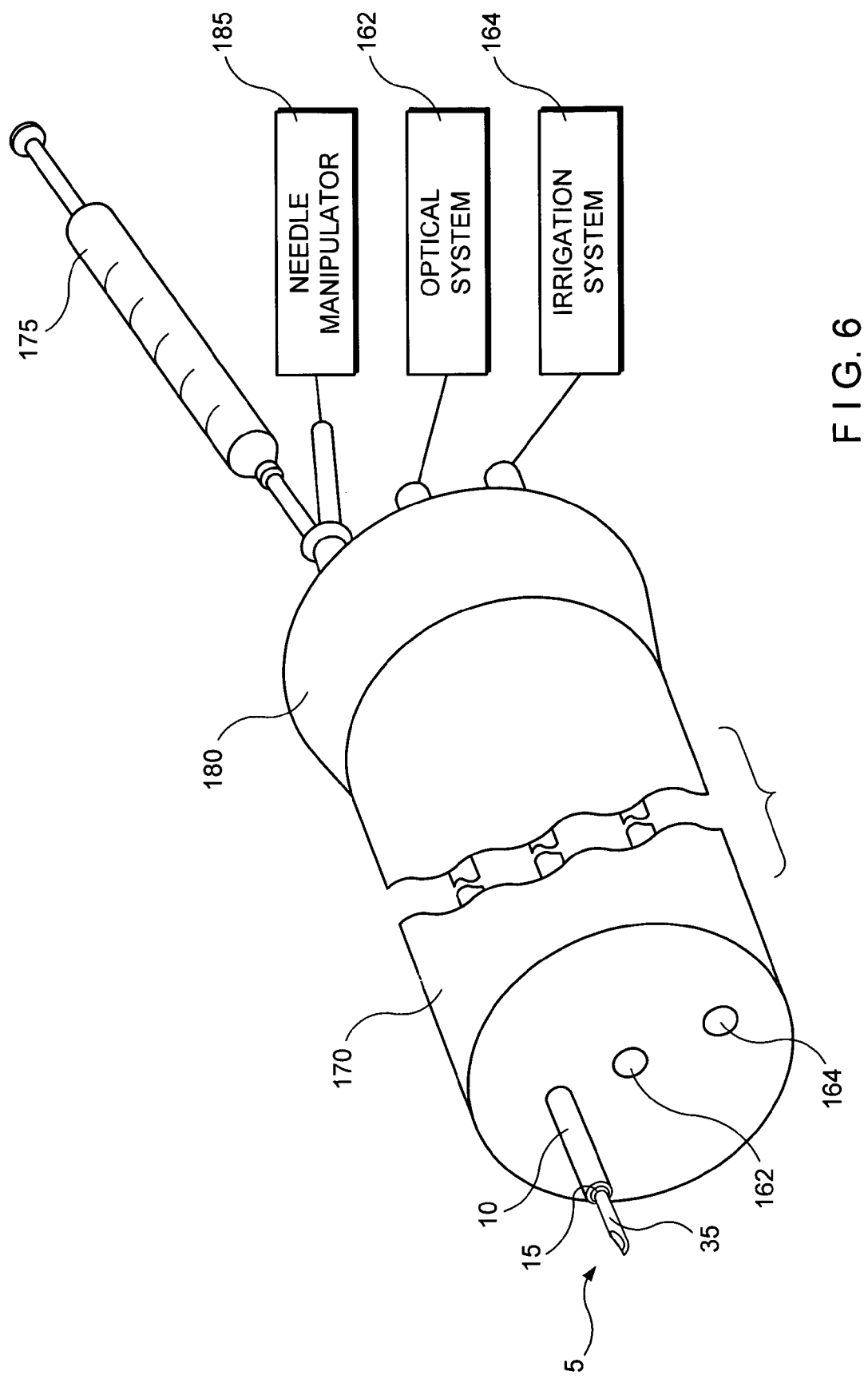

FLEXIBLE NEEDLE

BACKGROUND

Conventional sclerotherapy catheters include needles which are extendable and retractable beyond distal ends thereof. Such a catheter is typically inserted through an endoscope located at a desired position within the body. The catheter is pushed distally through the endoscope until a distal end of the catheter extends beyond a distal end of the endoscope. The needle is then extended from the catheter and inserted into the target tissue and a sclerosing agent is administered thereto to cause the target tissue to thicken or harden.

The needles typically utilized in conjunction with such sclerotherapy catheters are rigid, which hinders maneuverability of the catheters within endoscopes. Also, these needles often have a length of at least 1 cm to allow them to successfully puncture tissue and administer a sclerosing agent. The rigidity and length of the needles present difficulties in attempting to guide the sclerotherapy catheter through an endoscope and/or through a body lumen. That is, if advancing the catheter through an endoscope requires bending the sclerotherapy catheter around a tight radius, the needle may be exposed, puncturing the catheter and/or the endoscope. In some cases, the needle may prevent the sclerotherapy catheter from moving past the tight radius.

SUMMARY OF THE INVENTION

The present invention is directed to an endoscopic instrument comprising a first flexible insertion member sized for insertion through a body lumen to a target site and a needle coupled to the insertion member for penetration of tissue, the needle including a plurality of flexibility enhancing grooves formed therein along at least a first portion of the length of the needle.

BRIEF DESCRIPTION OF THE DRAWINGS

FIG. 3a shows a side view of an exemplary embodiment of a needle according to the present invention;

FIG. 3b shows a perspective view of the embodiment of the needle shown in FIG. 3a;

FIG. 4a shows a side view of a further exemplary embodiment of a needle according to the present invention;

FIG. 4b shows a perspective view of the embodiment of the needle shown in FIG. 4a;

FIG. 5a shows a side view of another exemplary embodiment of a needle according to the present invention;

FIG. 5b shows a perspective view of the embodiment of the needle shown in FIG. 5a; and FIG. 6 shows a perspective view of an exemplary embodiment of a system according to the present invention.

DETAILED DESCRIPTION

Figure 1:
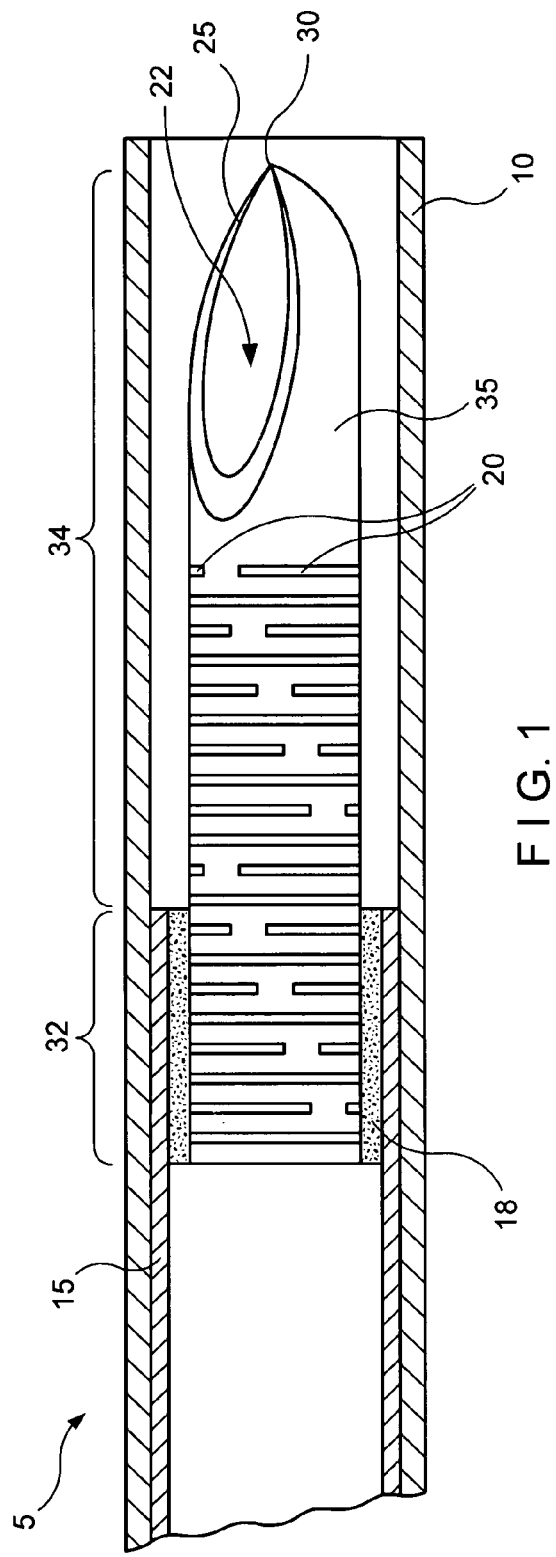
FIG. 1 shows a side view of an exemplary embodiment of a needle within a catheter according to the present invention.

The present invention may be further understood with reference to the following description and the appended drawings, wherein like elements are referred to with the same reference numerals. Although the present invention is described herein in reference to sclerotherapy, those skilled in the art will understand that a flexible needle constructed in accord with the present invention may be employed in any procedure which requires a needle with enhanced flexibility (e.g., for bending around a tight radius). Furthermore, although the present invention is described herein with specific reference to needles, those skilled in the art will understand that the teachings of the invention may be applied in the same manner to a wide range of items formed of rigid materials which are inserted through endoscopes. For example, hemaclips, Enteryx® needles, fine needles, aspiration needles, and coring needles for tissue acquisition may be made more flexible using the same processes described herein for the needle 35. Further, all gastrointestinal instruments and other medical instruments which are often formed of rigid materials to achieve a desired column strength but which are required to pass through a tortuous path to reach target tissue may be made more flexible using the teachings of the present invention.

As shown in FIG. 1, a catheter 5 includes an outer sheath 10 and an inner sheath 15. Both the inner sheath 15 and the outer sheath 10 may, for example, be formed of a plastic polymer tubing, although other materials having similar characteristics (e.g., flexibility, biocompatibility, etc.) may be used. A needle 35 is attached to inner sheath 15 by, for example, mechanically crimping a proximal end of the needle 35 to a distal end of the inner sheath 15. Alternatively or additionally, an adhesive 18 may be applied to the proximal end of the needle 35 to bond it to the inner sheath 15. A first predetermined length 32 of the needle 35 is inserted proximally into the inner sheath 15 leaving a second predetermined length 34 extending distally from the distal end of the inner sheath 15. In one embodiment, the first predetermined length 32 is approximately 3 to 4 mm, and the second predetermined length 34 is approximately 5 to 6 mm.

The inner sheath 15 is slidably received within a lumen of the outer sheath 10 so that a position of the outer sheath 10 relative to the inner sheath 15 may be manipulated by a user. During insertion and retraction of the catheter 5 through an endoscope, the outer sheath 10 is advanced distally relative to the inner sheath 15 until the distal end of the outer sheath 10 extends past a distal end of the needle 35 to protect the needle 35 and the endoscope by preventing the needle 35 from scraping, puncturing, or otherwise damaging a wall of the endoscope.

After the endoscope has been positioned in a desired location relative to the target tissue, the outer sheath 10 and the inner sheath 15 are advanced together to project distally from a distal end of the endoscope. The needle 35 is then exposed by withdrawing the outer sheath 10 proximally. Those skilled in the art will understand that alternatively, the needle 35 may be exposed by moving the outer sheath 10 and the inner sheath 15 together to the distal end of the endoscope and then extending the inner sheath 15 distally relative to the outer sheath 10. The inner sheath 15 and the outer sheath 10 are preferably moved relative to one another via an actuator which, during use, remains outside the body. The actuator may be any standard actuator, but may preferably be a one-hand operable device, such as a spool or finger loop handle as would be understood by those skilled in the art. Once exposed, the needle 35 is inserted into the target tissue by advancing the inner sheath 15 further distally. At this point, a therapeutic agent (e.g., a sclerosing agent) may be injected into the target tissue.

Successful insertion of the needle 35 into the target tissue may require the second predetermined length 34 of the needle 35 to be at least approximately 3 or 10 mm. Taking into account the 2 to 5 mm of needle length required for attachment to the inner sheath 15, a total length of the needle 35 is approximately 1.5 cm.

According to the present invention, a plurality of slots 20 are formed at predetermined locations on the needle 35 to enhance its flexibility. The slots 20 may preferably be formed by removing segments of the material comprising the needle 35 as described in more detail below. The slots 20 may be formed along the length of the needle 35 at regular intervals or may be spaced by variable distances, thereby increasing the flexibility of selected areas while leaving others relatively rigid. In addition, the slots 20 may be formed around an entire circumference of the needle 35 to achieve a substantially equal amount of flexibility in all directions or may be formed on one side only to allow greater flexibility in one direction than another. However, an embodiment where the slots 20 are formed circumferentially around the needle 35 may be preferable to achieve a substantially flexibility which is substantially uniform in all directions. This increased flexibility of the needle 35 facilitates navigation around tight bends in the endoscope, minimizing the risk of the needle 35 scraping or penetrating the wall of the endoscope.

The size and spacing of the slots 20 are selected to maintain a predetermined degree of axial strength sufficient to allow the needle 35 to be pushed through the turns required to navigate target pathways in the body and to penetrate the target tissue. Those skilled in the art will understand that the outer sheath 10 adds a degree of support to the needle 35 when the inner sheath 15 and the outer sheath 10 are advanced together. Thus the flexibility of the needle 35 may be increased to a level greater than would be feasible without the outer sheath 10.

The slots 20 in the first predetermined length 32 of the needle 35 may also receive the adhesive 18. The slots 20 act as a mechanical lock for the adhesive 18 to grip and hold, thereby providing a stronger attachment to inner sheath 15. Accordingly, the inner sheath 15 may be more securely bonded to the proximal end of a needle 35 with slots 20 than it would be to a typical medical needle. The slots 20 will retain flexibility where there is no adhesive or crimp. Consequently, however, the flexibility of the needle 35 may be decreased in the first predetermined length 32 relative to the second predetermined length 34 which is exposed. As this portion is only necessarily 2 to 5 mm in length, its decreased flexibility should not present a problem. Alternatively, the adhesive, crimp, or other attachment means may be made flexible, and thus even this portion of the needle 35 may be slotted so that this portion too will exhibit an increased degree of flexibility. However, those skilled in the art will understand that even in an embodiment where the attachment means is relatively stiff, the portion at which it is coupled to the inner sheath 15 is short enough to pass through even the tightest bends in a narrow lumen with relative ease.

The recommended method for creating the slots 20 is by using a computer-controlled slot grinding technology. The grinding technology utilizes a computer to control a length of a cut made in the needle 35. Preferably, this process is used to grind the slots 20 at a predetermined width (e.g., 0.003" to 0.004", which converts to approximately 0.075 mm to 0.10 mm). This process is described in detail in U.S. Pat. No. 6,766,720 the entire disclosure of which is hereby incorporated in its entirety by reference herein.

The slots allow a rigid material to exhibit flexible characteristics in a controlled manner. That is, portions of the rigid material can be selectively ground away, thereby creating slots, which may be sized and spaced to achieve a desired degree of flexibility while other areas are left relatively stiff or are made more or less flexible. In addition, by grinding on one side only, the material may be made flexible in one direction and relatively stiff in other directions. By locating slots only in selected areas along the axis of the needle 35, a desired flexibility may be obtained in those preselected sections of the needle 35 while maintaining rigidity in other areas of the needle 35. The grinding process may be performed on tubing of a relatively small diameter, as well as tubing of a much larger diameter. Furthermore, those skilled in the art will understand that, depending on the properties desired for the needle 35 or other instrument being formed, slots may be formed along helical paths, or substantially parallel to a longitudinal axis of the needle 35 or other instrument. In addition, the geometry of the slots may vary from slot to slot.

Although the computer controlled slot grinding may be used to create the slots 20 in the needle 35, other methods may be used. For example, in one embodiment, a laser may be used to make the slots 20. The laser may be employed to cut more intricate, complex shapes with precision and minimal damage (e.g. fracture) or distortion (e.g. compression) to the needle 35. Other methods which may be used to create the slots 20 in the needle 35 include drilling, high pressure water cutting, photo-etching, etc. In another embodiment of the present invention, the needle 35 and the slots 20 may be created by a molding process (e.g., injection molding, blow molding, etc.). That is, the needle 35 may be made of a strong and/or reinforced polymer. Thus, the slots 20 would be positioned, sized, and shaped in accordance with a pattern defined by the molding process.

In a preferred embodiment, the needle 35 is made of a shape-memory alloy (e.g. nitinol hypodermic tubing) or of a similar material that has a high tensile strength. The high tensile grade of nitinol makes this type of needle 35 easier to work with than one composed of other materials, because nitinol can withstand high amounts of flexing without fracture or permanent flexion under normal working conditions. Although nitinol is the preferred material for composition of the needle 35, other materials are suitable and compatible with the computer controlled grinding process. For example the grinding process may be performed on stiff polymers (e.g. plastic polyimids), reinforced materials, stainless steel braided reinforced tubing, etc.

Figure 2:
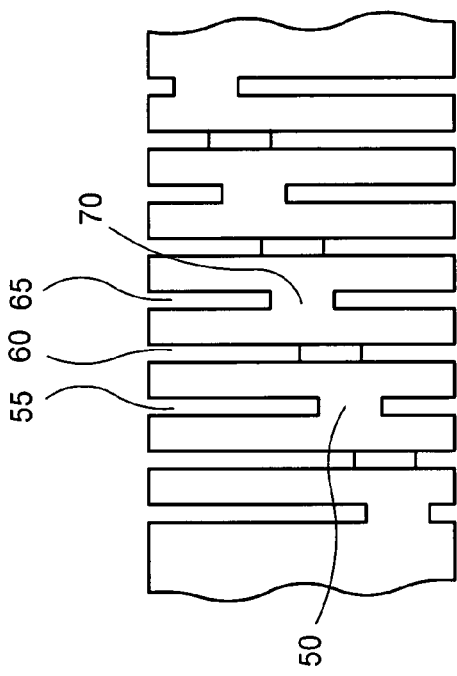
FIG. 2 shows a detail view of the needle according to the present invention.

As would be understood by those skilled in the art, the flexibility of the needle 35 may be manipulated through variation of the shape and position of the slots 20. FIG. 2 depicts a pattern formed by grinding a plurality of slots 20 along the needle 35, thereby excising partial circumferential sections of the needle 35. These partially circumferential excisions are placed at predetermined intervals along the length of the needle in such a way as to increase flexibility while maintaining a high degree of strength. Regarding FIG. 2, narrow circumferential sections 55 are removed from the needle 35 so that a segment 50 is left intact to keep the distal end of the needle 35 from being completely severed from the proximal end. In the adjacent excision 60, the segment left intact is located approximately directly opposite the original remaining segment 50 with respect to a longitudinal axis of the needle 35. The next adjacent partial circumferential excision 65 is positioned such that the remaining segment 70 is roughly even with the original remaining segment 50, but slightly vertically displaced therefrom. As shown in FIG. 2, a pattern is formed in the needle 35 by the slots 20 such that the remaining segments are substantially evenly distributed along the axis and wrapping around the body of the needle 35, along a substantially helical path. This pattern produces a degree of flexure that is suitable for navigating through an endoscope and a body lumen and which is substantially equal in all directions.

The slots 20 as described above with respect to FIGS. 1 and 2 may optionally penetrate all the way to the bore 22 of the needle 35. Alternatively, the depth of the slots 20 may be less than a thickness of a wall of a hollow needle 35. When the depth of the slots 20 is less than a thickness of the wall of the needle 35, the wall of the needle 35 is substantially thinned at the slots 20 relative to other sections of the needle 35 and therefore increases a degree of flexibility of these portions of the needle 35 while maintaining the integrity of the inner lumen of the needle 35. This allows a more precise control of the locations at which a fluid supplied to the inner lumen of such a needle 35 would be delivered. Furthermore, as the thinner section still connects the distal end of the needle 35 to the proximal end, such slots 20 may if desired be formed fully circumferentially. This embodiment therefore provides increased flexibility without creating porosity in the needle 35. Those skilled in the art will understand that the depth of the slots may be varied along the length of the needle 35 to achieve any desired flexibility and/or fluid delivery characteristics along the length of the needle 35.

As illustrated in FIG. 2, the slots are created in a substantially rectangular shape that extends over a substantial portion of the circumference of the needle 35. However, the slots may take alternative forms (e.g. elliptical, polygonal, etc.) and may be sized to extend over varying portions of the circumference of the needle 35. Variations in the size or shape of the slots may have a corresponding effect on the flexibility of the needle 35.

As the size and shape of the slots 20 may affect the flexibility characteristics of a needle 35, the placement and separation between the slots 20 may also have a substantial effect. For instance, a plurality of slots 20 concentrated in one portion of the needle 35 may substantially increase the flexibility of the needle 35 in that portion. However, that portion of the needle 35 will also lose a degree of longitudinal rigidity. Conversely, if the same number of slots 20 are positioned at a greater distance from one another along a longer section of the needle 35. However, the entire needle 35 will have a level of flexibility higher than that of the areas of this needle 35 outside the area of dense slot concentration. The needle 35 will not have any section as flexible as the area of dense slot concentration described above.

The slots 20 illustrated in FIGS. 1 and 2 are positioned in planes substantially perpendicular with respect to the longitudinal axis of the needle 35. In an alternative embodiment, the slots 20 may extend in planes orientated at various angles with respect to the longitudinal axis. A preferred range of angles with respect to the longitudinal axis of the needle 35 may be between approximately 45° and 90°.

Referring back to FIG. 1, the needle 35 has a distal tip 30 which facilitates penetration into target tissue. The needle 35 also includes a hollow bore 22, through which a fluid may pass proximally or distally. In sclerotherapy, for example, fluid exits the needle 35 at an outlet near the tip 30. Accordingly, once the needle 35 has been inserted into target tissue, an agent is injected thereinto from the distal end of the needle 35. Due to the nature of its release, the stream of injected fluid immediately comes into contact with the portion of target area toward which the needle 35 is pointing. From there it spreads to the rest of the target tissue. An advantage of the flexible needle of the present invention is that fluid may also exit through the slots 20 formed along the length of the needle 35, dispersing the fluid more widely throughout the target tissue.

If it is desired to have a needle 35 which is flexible but not porous, any slots 20 which penetrate to the bore 22 may be sealed. In one embodiment of the present invention, the slots 20 may be sealed by dipping the needle 35 in a soft polymer. The polymer preferably covers the slots 20 without obstructing the bore 22. As a result, a needle 35 sealed with a thin polymer coating and having an outlet at the distal end will possess substantially the same flexibility characteristics as the porous needle 35 described above. In another exemplary embodiment, a thin sheath may be slidably received around the needle 35, thereby sealing the slots 20. As would be understood by those skilled in the art, the sheath may be formed to impart a selected degree of rigidity to the needle 35 so that the needle 35 will retain a desired degree of flexibility.

As shown in FIGS. 3, 4, and 5, the distal end of the needle 35 may be contoured to take a form most suitable for a desired application. FIG. 3 depicts a needle 82 having a regular medical point, or a "lancet point." The distal end of the needle 82 is shaped to form a sharp point 90. As shown in FIG. 3, a sharp cutting edge 85 is formed at an angle (e.g. approximately 15 degrees) with respect to a longitudinal axis of the needle 82. Preferably, the angle of the sharp cutting edge 85 may be approximately equivalent to a diameter of the needle 35 divided by a length of the sharp cutting edge 85. The sharp cutting edge 85 meets a heel 80 of the lancet point. The heel 80 may be formed at an angle, with respect to the longitudinal axis of the needle 35, that is smaller than the angle formed by the sharp cutting edge 85 as per standard needle specifications in the industry.

FIG. 4 depicts a needle 102 having a deflected point 105 reducing possibility of puncturing a lumen wall of an endoscope as the needle 102 is advanced therethrough. The deflected point 105 also aids in keeping the bore 110 of the needle 102 unobstructed. For example, when injecting a lancet point needle 82 such as that shown in FIG. 3 into target tissue, the large diameter of the outlet in connection with the sharp cutting edge 85 may cause a section of tissue approximately the diameter of the needle 82 to be removed. The removed tissue section may then become lodged in the needle bore 95 leaving a hole in the target tissue. The deflection of the point 105 in FIG. 4 displaces the point 105 toward the sharp cutting edge 100. Accordingly, the outlet of the hollow bore 110 is more closely aligned with the longitudinal shape of the needle 102. As the point 105 lies nearly on the same plane as an opposite surface of the needle 102, and the sharp cutting edge 100 does not directly abut a surface of the target tissue, the needle 102 penetrates tissue more smoothly. The diameter of the hole created in the tissue by the puncture gradually increases to the diameter of the needle 102 as the needle 102 is inserted without removing a section of tissue. Thus, the hole will close and the tissue will heal more readily.

FIG. 5 portrays a needle 122 with a deflected guide tip 125. This needle 122 retains all the benefits of the needle 102 of FIG. 4. For example, the outlet of a hollow bore 130 is more closely aligned with a longitudinal shape of the needle 122, and therefore a sharp cutting edge 120 does not directly abut a surface of the target tissue, enabling smooth penetration of the needle 122. Additionally, the tip 125 of this needle 122 is curved towards axis of the needle 122 reducing risk of damaging the lumen wall as the needle 122 is passed through the endoscope.

In an alternative embodiment shown in FIG. 6, an injection catheter 5 is slid through the working channel 165 of an endoscope 170 which may be, for example, a standard endoscope including, for example, devices such as an irrigation system 164 and at least one optical system 162 to facilitate insertion of the endoscope 170, positioning, and performance of the procedure. The endoscope 170 may be a single use endoscope or a conventional multi-use endoscope. The endoscope 170 is placed within a body lumen (e.g., through a naturally occurring orifice) and positioned proximate to a target area. The optical system 162, the irrigation system 164, and a syringe 175 are connected to the endoscope 170 through a medical luer adaptor 180, as would be understood by those skilled in the art. The injection catheter 5 includes a needle 35 attached to an inner sheath 15, within an outer sheath 10. As with conventional sclerotherapy needles, the needle 35 is extended and retracted as necessary via a manipulator 185 located at the proximal end of the endoscope 170. The manipulator 185 may be a one-hand or two-hand operable device. Additionally or alternatively, the manipulator 185 may be automatic and/or computer controlled. When in the retracted position, the needle 35 is housed within the outer sheath 10. As the needle 35 is extended and exposed from the distal end of the outer sheath 10, the user may insert the needle 35 into the target tissue and inject fluid from syringe 175 into the target tissue. After the fluid has been administered to the target tissue, the needle 35 is retracted and withdrawn through the endoscope 170.

In another exemplary embodiment of the present invention, the needle 35 and/or the injection catheter 5 may be part of the endoscope 170. That is, the needle 35 and/or the injection catheter 5 may be a permanent fixture of the endoscope 170. This embodiment may be practical with respect to incorporating the present invention into a single-use endoscope.

In another exemplary embodiment of the present invention, the needle 35 may be part of an endoscopic accessory. For example, the needle 35 may be part of a cup attached to a distal end of an endoscope (e.g., via a snap-on linkage) with a generic device connection linking the needle 35 to an actuator or controller of the endoscope. For example, the needle 35 may be connected to a control wire extending between a distal end of the endoscope and a proximal actuator of the endoscope.

The present invention has been described with reference to specific exemplary embodiments. Those skilled in the art will understand that changes may be made in details, particularly in matters of shape, size, material and arrangement of parts without departing from the teaching of the invention. Accordingly, various modifications and changes may be made to the embodiments without departing from the broadest scope of the invention as set forth in the claims that follow. The specifications and drawings are, therefore, to be regarded in an illustrative rather than a restrictive sense.

What is claimed is:

1. An endoscopic instrument comprising:
    a first flexible insertion member sized for insertion through a body lumen to a target site; and
    a needle coupled to the insertion member for penetration of tissue, the needle including a plurality of flexibility enhancing grooves formed therein along at least a first portion of the length of the needle, wherein at least one of the grooves comprises a first needle wall thickness that is less than a second needle wall thickness at a portion of the needle in which the grooves are absent, the first needle wall thickness at the at least one of the grooves preventing fluidic communication between a bore of the needle and the at least one of the grooves, and wherein each of the grooves extends around only a part of a circumference of the needle so that midpoints of the groove extend along a substantially helical path.

2. The instrument of claim 1, wherein the bore extends axially through the needle, at least a first one of the grooves penetrating from an outer surface of the needle to the bore.

3. The instrument of claim 2, wherein the bore extends to a distal opening for the injection of fluids to penetrated tissue, fluids also being supplied to tissue via the first groove.

4. The instrument of claim 1, wherein the grooves are formed in a plane substantially perpendicular to a longitudinal axis of the needle.

5. The instrument of claim 1, wherein the grooves are positioned substantially equidistant from one another.

6. The instrument of claim 1, wherein a spacing between the grooves varies along the length of the first portion.

7. The instrument of claim 1, wherein the first insertion member is sized to be inserted through a working channel of an endoscope.

8. The instrument of claim 1, further comprising a second flexible insertion member, the first insertion member being slidably received within the second insertion member.

9. The instrument of claim 1, the first insertion member being formed of a first material and the needle being formed of a second material more rigid than the first material.

10. The instrument of claim 1, further including a non-porous coating covering the first portion of the length of the needle.

11. The instrument of claim 10, wherein the coating is an adhesive that covers at least one but less than all of the grooves and adheres the needle to the first insertion member at a location of the less than all the grooves covered by the adhesive.

12. The instrument of claim 1, wherein a distal most tip of the needle bends toward a longitudinal axis of the needle.

13. A method of forming a needle for use in endoscopic procedures comprising:
    fabricating a needle of a material having a first stiffness;
    forming a plurality of grooves in at least a first portion of the needle to increase the flexibility of the first portion, wherein at least one of the grooves comprises a first needle wall thickness that is less than a second needle wall thickness at a portion of the needle in which the grooves are absent, the first needle wall thickness at the at least one of the grooves preventing fluidic communication between a bore of the needle and the at least one of the grooves, and wherein each of the grooves extends around only a part of a circumference of the needle so that midpoints of the groove extend along a substantially helical path.

14. The method of claim 13, wherein at least a first one of the grooves penetrates from an outer surface of the needle to the bore extending axially therethrough.

15. The method of claim 13, wherein the grooves are formed in a plane substantially perpendicular to a longitudinal axis of the needle.

16. The method of claim 13, wherein the grooves are positioned substantially equidistant from one another.

17. The method of claim 13, wherein a spacing between the grooves varies along the length of the first portion.

18. The method of claim 13, further comprising applying a non-porous coating to the first portion of the needle.

19. The method of claim 18, wherein the coating is an adhesive that covers at least one but less than all of the grooves and adheres the needle to a first insertion member at a location of the less than all the grooves covered by the adhesive.

20. The method of claim 13, wherein the needle is fabricated to have a distal most tip that bends toward a longitudinal axis of the needle.

* * * * *